US00PP11132P

United States Patent [19]

Saville

[11] Patent Number: Plant 11,132

[45] Date of Patent: Nov. 23, 1999

[54] MINIATURE ROSE PLANT NAMED 'SAVALUTE'

[75] Inventor: F. Harmon Saville, deceased, late of Newburyport, Mass., by Charles K. Brown, executor

[73] Assignee: Nor'East Miniature Roses, Inc., Rowley, Mass.

[21] Appl. No.: 08/993,378

[22] Filed: Dec. 18, 1997

[51] Int. Cl.[6] ..... A01H 5/00

[52] U.S. Cl. ..... Plt./123

[58] Field of Search ..... Plt./123, 116, 128, Plt./125, 118, 121

*Primary Examiner*—Howard J. Locker

[57] ABSTRACT

SAValute is a miniature rose which can be grown quite satisfactorily in a greenhouse, or as a hardy garden perennial. It blooms continually throughout the growing season with buds and flowers of a yellow and apricot blend. Blooms are borne singly and in small sprays on a vigorous, upright and spreading plant up to about 2 feet tall and with a diameter of 30 inches or more.

1 Drawing Sheet

BACKGROUND OF THE INVENTION

1. This invention is a rose plant of the miniature rose class which can be grown quite satisfactorily in a greenhouse and as a garden perennial, with protection recommended through the winter in severe climates.

2. The present invention is a new and distinct variety of miniature rose plant (*Rosa chinensis* 'minima'), which was created by crossing the following two rose plants: The seed parent is an unnamed and unpatented seedling, red with a white eye in color, created by F. Harmon Saville in 1975. The pollen parent is Rise 'N Shine (U.S. Plant Pat. No. 4,231, also known as Golden Meillandina and Golden Sunblaze, created by Ralph Moore) a clear yellow medium sized miniature. The varietal denomination of this new rose is SAValute.

3. This present invention relates to a new and distinct variety of hardy, bush type plant of the miniature rose class, whose flower and coloring are similar to those of Party Girl (U.S. Plant Pat. No. 4,598, created by F. Harmon Saville in 1979) having a pale yellow flower with apricot and or pink tones and beginning with a high centered form, and with which it shares the common parent plant Rise 'N Shine (U.S. Plant Pat. No. 4,231 also known as Golden Meillandina and Golden Sunblaze) which has a medium yellow flower.

This new variety is distinguished by:

A. Its pale and medium yellow blooms always flushed with apricot.
B. Miniature flowers of Hybrid Tea form, borne singly and in small sprays.
C. A vigorous, well branched, upright, somewhat compact and spreading habit.
D. Its pleasant fragrance.

Asexual reproduction by cuttings of this new variety as performed in Essex County, Mass. and in San Bernadino County, Calif. shows that all distinguishing characteristics of this rose continually come true to form.

SUMMARY OF THE INVENTION

This new variety has light and medium yellow flowers flushed lightly on the outer edges with an orange-red giving the appearance of being a pale apricot and apricot-pink as it blends with the yellows. Occasionally some flowers will be somewhat darker shades of the same coloring or have a different petal count, both or either on the same plant at the same time, but never in the same spray and rarely on the same lateral. The open flowers have a slight fragrance. Blooms are borne singly and in small sprays of 3 to 5. The plant itself has relatively few thorns, is vigorous, well branched and somewhat compact yet spreading to 30 inches and growing to 2 feet tall at maturity. It can be grown quite satisfactorily in a greenhouse or as a hardy garden perennial requiring winter protection in severe climates.

BRIEF DESCRIPTION OF THE DRAWING

The accompanying color photograph shows specimens of the flowers of this new variety in different stages of development as seen and grown inside under plastic in September in Essex County, Mass.

BOTANICAL DESCRIPTION OF THE PLANT

Following is a detailed description in outline form pertaining specifically to this new and distinct variety of miniature rose plant. All major color plate identifications made are referring to The Royal Horticultural Society Colour Chart except where common terms of color definition are employed.

Type: Miniature rose: hardy; outdoors; decorative; potted plant; greenhouse.
Seed parent: Unnamed seedling.
Pollen parent: Rise 'N Shine, U.S. Plant Pat. No. 4,231, also sold and marketed as Golden Meillandina and Golden Sunblaze.
Flowers: Borne singly and in small sprays.
Quantity of bloom: profuse.
Bud:

*Size and form.*—Medium, ovate with an acute tip.

*Sepals.*—Lanceolate, 2 inner sepals very finely bearded, 2 outer sepals have many protrusions, 1 outer sepal is half and half, all extending beyond the tip of the bud; between 144B and 144C in color; rolling back gently before the petals start to unfurl and then back to the stem when the bloom is fully open, remaining permanently attached and drying and dropping with the peduncle, or rolling back upwards slowly as the hip forms.

*Color when sepals first divide.*—Near 11D or sometimes near 14Cand near 14D and always with edges flushed lightly with near 42D.

*When petals begin to unfurl.*—Colors remain unchanged.

*Peduncle.*—Varying from 5/8 to 1 3/8 inches; straight: erect; near 145A in color and flushed lightly with 40D.

Bloom:

*Size when fully expanded.*—To 2 inches.

*Form.*—High centered at first, petals becoming and remaining loosely rolled outward.

*Petalage under normal conditions.*—May be 22 to 27 petals with 0 to 5 petaloids in the center or 30 to 40 petals with 6 to 10 petaloids in the center and both appearing on the same plant but never within the same spray and not usually on the same lateral.

*Fragrance.*—Slight.

Petals:

*Texture.*—Medium; inside and outside velvety.

*Form.*—Spatulate.

*Arrangement.*—Petals overlapping in an irregular pattern.

*Color.*—(From plants grown inside under plastic in Essex County, Mass., in September, 1997):

*During first two days.*—usually: (outer petals) inner surface — near 12B at base and becoming 11B at tip flushed lightly with near 35C from outer edges inward; reverse — near 15C at base and becoming near 11C at tip. (inner petals) inside surface — near 12A at base becoming near 11A toward tip and flushed lightly with near 35C; reverse — near 13C at base becoming near 11B towards tip with very edges flushed with near 35C; and ocassionally: (outer petals) inside surface — near 15C at base and becoming near 20B at tips and edges flushed with near 35B; reverse — near 13B at base becoming near 14C at edges. (inner petals) inside surface — near 15B and edges flushed with near 40D; reverse — near 13B and edges flushed with near 40D.

*When half blown.*—usually: (outer petals) inside surface — near 6D at base and becoming near 4D at tips and edges flushed lightly with near 35B and near 35C; reverse — near 6D and edges flushed with near 35C. (inner petals) inside surface — near 9C at base and becoming near 9D at tips and edges flushed lightly with near 35D; reverse — near 10C at base and becoming 11C at tips with edges flushed with near 35C. and occasionally: (outer petals) inside surface — near 12B at base and becoming near 11D at tips and edges flushed lightly with near 43D; reverse — near 12C at base and becoming near 11D at tips and edges flushed lightly with near 43D. (inner petals) inside surface — near 12A and flushing from edges inward with near 43D; reverse — near 12C and very edges of near 43D and appearing flushed with 35B where the 43D shows through from the inside surface.

*Base of petals at attachment.*—near 15A.

*Color change as bloom ages.*—Light yellow blooms, slightly darker towards the center of the flower and flushed at the edges with a light red become uniformly lighter as the flower ages, sometimes having flowers of a slightly darker shade of yellow on the same plant at the same time. More specifically one of the following two colorations: most often from near 11D and edges flushed with near 42D before petals start to unfurl; to near 11B with 11A towards the center flushed lightly with near 35C; to near 4D flushed with near 35D and 35C and near 9D towards the center and edges flushed with 35B; or occasionally on the same plant from near 14C at the base and near 14D toward the upper edges and flushed wth near 42D before petals start to unfurl; to outer petals of near 20B and flushed lightly with near 35B and inner petals near 15B and edges flushed with near 40D; to outer petals of near 11D flushed lightly with near 43D and inner petals of near 12A flushed lightly with near 35B; and both colorations becoming all near 8D and edges or entire surface flushed lightly with near 35D.

*General tonality.*—Yellow and apricot-pink blend; after three or more days — lighter shades of the same coloring.

Lasting quality:

*On plant.*—5 or more days, and petals often remaining attached and dropping with peduncle after both have dried or if a hip is forming the petals dry and drop before the hip is fully developed.

*As a cut flower.*—4 to 7 days.

Reproductive organs:

*Stamens.*—Few; one thin row along upper, outer edge of receptacle.

*Filaments.*—Varying from 1/16 to 3/16 of an inch; near 14B in color.

*Anthers.*—Near 16D in color.

*Pollen.*—An ample amount; near 17A in color.

*Pistils.*—Few.

*Styles.*—Undulating stems up to 3/16 of an inch in one small bunch; color near 150D.

*Stigmas.*—color near 9D.

*Hips.*—Pear shaped, up to 7/16 of an inch; only observed to a dark green color.

*Seeds.*—Seeds are small, several per hip with none protruding.

The plant:

*Habit.*—Spreading, upright, well branched, compact.

*Growth.*—Very vigorous, uniformly branched, 20 to 24 inches tall and spreading to a 30 inch diameter.

*Foliage.*—Medium, abundant, compound of five to seven and occasionally 3 leaflets. Color: new foliage, upper surface — near 144A and margins flushed with near 183A; under side — between near 144A and 144B and flushed with near 183A. Old foliage, upper surface — near 147A; underside — near 147B.

*Thorns, prickles or hairs.*—0 to few prickles, some small hairs on underside of main leaf stem.

*Leaflet.*—Shape — oval pointed; texture, upper surface — (semi glossy new growth) matte older growth, under side — matte; edge — fine serration, nearly even on right side of leaflet; uneven on left side.

*Rachis.*—Color, upper surface — near 146B flushed very lightly with near 183C; underside — near 146C flushed lightly with near 183C.

*Stipules.*—Nearly even in length, about 1/8 of the length of the mature leaf; slightly bearded.

*New wood.*—Smooth, between near 144A and near 146B flushed with near 183B.

*Old wood.*—Between near 143C and 144B and with slightly raised areas of near 166D.

*Thorns.*—3/16 to 5/16 of an inch long, thin, very pointed, straight and angled down. On main stalk: none. On laterals from main stalk: very few.

*Prickles.*—Only 0 to few on the underside of the main stem of each leaf.

*Resistance to diseases*.—This new invention is tolerant of Blackspot and Downy Mildew. No Rust hass been observed on this cultivar.

The miniature rose plant and its flowers described herein may vary in detail due to climate, soil and cultural conditions under which the variety may be grown; the present description being of the new variety as grown inside under plastic in Essex County, Mass. in September.

The following is claimed:

1. A new and distinct variety of miniature rose plant of hardy, well branched, upright, spreading and compact habit, substantially as illustrated and described, characterized by medium sized blooms of light and medium yellow and flushed lightly on the outer edges with an orange-red that gives the appearance of being a pale apricot and apricot-pink as it blends with the yellows, and occasionally some flowers being somewhat darker shades of the same coloring or having a different petal count, both or either on the same plant at the same time, but never in the same spray and rarely on the same lateral; borne singly and in small sprays with a slight fragrance, and a plant with relatively few thorns; vigorous and spreading to 30 inches and growing to 2 feet tall at maturity; and easy to propagate from cuttings.

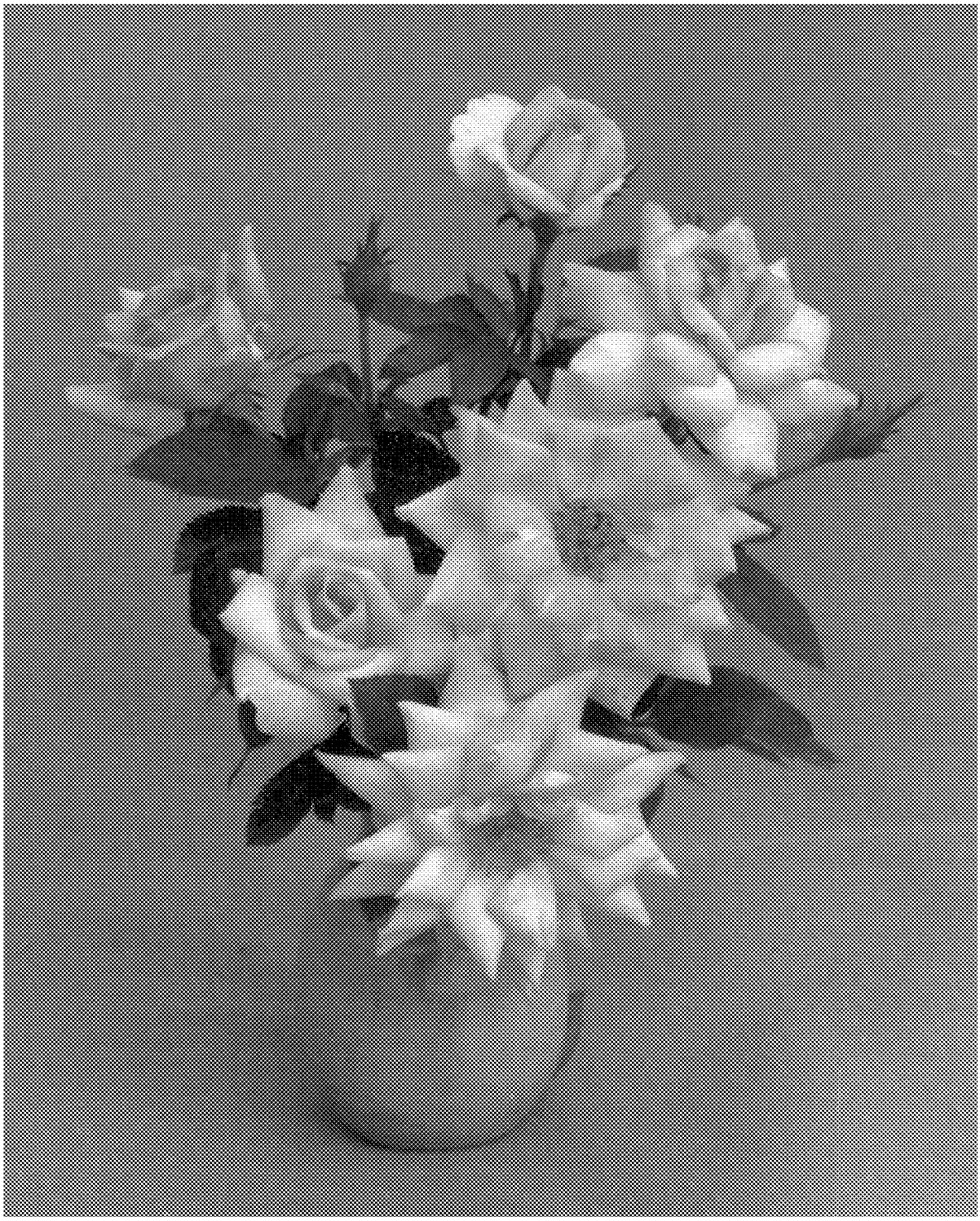

* * * * *